US006311546B1

United States Patent
Dickinson et al.

(10) Patent No.: US 6,311,546 B1
(45) Date of Patent: Nov. 6, 2001

(54) BIOFOULING MONITOR AND METHODS TO MONITOR OR DETECT BIOFOULING

(75) Inventors: Wayne H. Dickinson, Olive Branch, MS (US); Thomas E. McNeel, Memphis, TN (US); Richard A. Clark, Collierville, TN (US); E. Van Haute, Ghent (BE)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

(21) Appl. No.: 09/209,453

(22) Filed: Dec. 11, 1998

(51) Int. Cl.[7] .............................. G01M 3/02; G01N 7/00
(52) U.S. Cl. .................... 73/37; 73/61.62; 73/866.4; 73/53.01; 73/61.73; 436/148; 165/11.1
(58) Field of Search .................... 73/61.62, 112, 73/37, 53.01, 54.09, 61.68, 61.73, 866.4; 165/11.1; 422/82.13, 244; 436/6, 148

(56) References Cited

U.S. PATENT DOCUMENTS

| 3,141,324 | * | 7/1964 | Boies et al. ...................... 73/61.62 |
| 4,176,544 | | 12/1979 | Eyles et al. ...................... 73/61.2 |
| 4,599,217 | * | 7/1986 | Winston et al. ................... 73/866.4 |
| 4,686,853 | | 8/1987 | Sugam et al. ...................... 73/61.2 |
| 4,686,854 | * | 8/1987 | Herman ............................. 73/61.62 |
| 5,190,728 | | 3/1993 | Robertson et al. ................. 422/68.1 |
| 5,246,560 | | 9/1993 | Nekoksa et al. .................... 204/400 |
| 5,285,162 | | 2/1994 | Davies .............................. 324/425 |
| 5,356,521 | | 10/1994 | Nekoksa et al. .................... 204/153 |
| 5,411,666 | | 5/1995 | Hollis et al. ...................... 210/632 |
| 5,531,103 | * | 7/1996 | Eaton ............................... 73/61.62 |

FOREIGN PATENT DOCUMENTS 0 226 856 A2   7/1987 (EP) .............................. G01N/33/18

OTHER PUBLICATIONS

Lee, et al. "On–Line Monitoring and Quantitative Analysis of Biofouling in Low–Velocity Cooling Water System" *Korean J. Chem. Eng.*, vol. 15 No. 1, pp. 71–77 (1998).
Yoshihara K. Hakkokogaku Kaishi 60 (5). 182 pp. 349–354.*

* cited by examiner

*Primary Examiner*—Hezron Williams
*Assistant Examiner*—Michael Cygan
(74) *Attorney, Agent, or Firm*—Kilyk & Bowersox, P.L.L.C.

(57) ABSTRACT

A biofouling monitor is described which has a column having an inlet and an outlet; a microorganism nutrient feed line located upstream of the inlet; and a first pressure sensor located upstream of the inlet for measuring flow pressure and a second pressure system located downstream of the outlet for measuring flow pressure. Also described is a biofouling monitor which further has a recirculation system and optionally inert packing material located in the column. A method to monitor or detect biofouling ahead of time in an aqueous system is further described.

22 Claims, 7 Drawing Sheets

BIOFOULING MONITOR AND METHODS TO MONITOR OR DETECT BIOFOULING

BACKGROUND OF HE INVENTION

The present invention relates to the biofouling of various systems containing aqueous solutions and more particularly relates to monitors to detect or record biofouling and methods of monitoring or detecting biofouling.

Biological fouling on surfaces is a serious economic problem in many commercial and industrial aqueous process and water handling systems. The fouling is caused by a biomass which is the buildup of microorganisms and/or extracellular substances and by dirt or debris that become trapped in the biomass. Bacteria, fungi, yeasts, diatoms and protozoa are only some of the organisms which cause buildup of a biomass. If not controlled, the biofouling caused by these organisms can interfere with process operations, lower the efficiency of processes, waste energy, and reduce product quality.

Cooling water systems used in power-generating plants, refineries, chemical plants, air conditioning systems and other commercial and industrial operations frequently encounter biofilm problems. Biofilm is the buildup of layers of organisms. Cooling water systems are commonly contaminated with airborne organisms entrained by air/water contact in cooling towers as well as waterborne organisms from the systems makeup water supply. The water in such systems is generally an excellent growth medium for these organisms. If not controlled, the biofilm biofouling resulting from such growth can plug towers, block pipelines, and coat heat transfer surfaces with layers of slime, and thereby prevent proper operation and reduce equipment efficiency.

Industrial processes subject to problems with biofouling include those used for the manufacture of pulp, paper, paperboard, and textiles, particularly water laid nonwoven fabrics. For example, paper machines handle very large volumes of water in recirculating systems called "white water systems". The white water contains a pulp dispersion. The furnish to a paper machine typically contains only about 0.5% of fibrous and non fibrous paper making solids, which means that for each ton of paper, almost 200 tons of water pass through the paper machine, most of it being recirculated in the white water system.

These water systems provide an excellent growth medium for microorganisms, which can result in the formation of microbial slime in headboxes, water lines, and papermaking equipment. Such slime masses not only can interfere with water and stock flows, but when they break loose, can cause spots or holes in the paper as well as web breaks that cause costly disruptions in paper machine operations.

The control of microbial activity has traditionally been the province of toxic chemicals. U.S. Pat. Nos. 3,959,328, 4,054,542, and 4,285,765 are illustrative of the methods that rely on killing the offending microorganisms with toxic chemicals. Such method shave received the majority of the research effort because of the logic of eliminating the problem by eliminating the offending organism and because of the large number of available organic and inorganic chemicals that will kill microorganisms.

Several attempts to control the negative effects of biological activity either avoid the use of toxic chemicals or mitigate their use or impact on the environment. For instance, U.S. Pat. Nos. 3,773,623 and 3,824,184, both to Hatcher et al., relate to the use of the enzyme levan hydrolase to control the formation of bacterial slime in industrial water systems.

While efforts are continually made to control or prevent biofouling, the water systems, and especially the industrial water systems, still need to be shut down for cleaning or removal of the biofouling that has built up and which was not prevented by the introduction of biofouling control compositions. Although the introduction of microbicidal or anti-fouling compositions reduces the number of times a system has to be shut down for cleaning, it would be beneficial to have a biofouling monitoring system which enables the users to determine when biofouling has reached levels which require a shut down and cleaning. Otherwise, if users of the water systems are not aware of the biofouling buildup, such biofouling can result in poor quality products being made such as paper having spots or holes or could even be more detrimental such as a clogging of various lines used to supply feedstock to the water system. Thus, it is most preferred to have an early warning system which informs the users of the water systems of a potentially biofouling situation which needs correction either by the introduction of more chemicals or a shut down. If the users of the water systems know in advance that a shutdown is necessary, then plans can be made ahead of time to finish, for instance, a paper run or to increase the amount of chemicals in the water system to avoid poor quality products or damage to equipment in the water systems.

SUMMARY OF THE INVENTION

A feature of the present invention is to provide a biofouling monitor and methods to detect or monitor biofouling.

Another feature of the present invention is to provide a biofouling monitor system that will detect or monitor biofouling ahead of time in order for corrective measures to be taken.

Additional features and advantages of the present invention will be set forth in part in the description which follows, and in part will be apparent from the description, or, may be learned by practice of the present invention. The objectives and other advantages of the present invention will be realized and obtained by the disclosure particularly pointed out in the written description and the pending claims.

To achieve these and other advantages and in accordance with the purposes of the present invention, as embodied and broadly described herein, the present invention relates to a biofouling monitor which has a column having an inlet and an outlet. The monitor also has a microorganism nutrient feed line located upstream of the inlet and also has a first pressure sensor located upstream of the inlet for measuring flow pressure and a second pressure sensor located downstream of the outlet for measuring flow pressure.

The present invention further relates to a biofouling monitor which has the above components, namely the column, microorganism nutrient feed line and pressure sensors, as well as a recirculation system connected to the inlet. This recirculation is located downstream of the feed line and is also connected to the outlet for maintaining a pressure feed through the column. In this embodiment, the biofouling monitor also has an inert packing material located in the column. The amount of inert packing material in the column is present in an amount to still permit the passing of liquid containing material through the column.

In addition, the present invention relates to a method to monitor or detect biofouling ahead of time in an aqueous solution. The method includes passing at least a portion of the aqueous solution though a column having an inlet and an outlet. The aqueous solution is generally passed though the column on a continuous basis. A microorganism nutrient is introduced into a portion of the aqueous solution at a point upstream of the inlet. The flow pressures of the portion of the aqueous solution passing through the column are measured at a first point before the inlet and at a second point after the inlet on a continuous or non-continuous basis, and, the pressure differential based on these measurements is determined. From these pressure differential measurements, the amount of biofouling occurring can be monitored and plotted and a determination can be made whether biofouling is occurring or whether any biofouling that exists is increasing in the aqueous system. The microorganism nutrients being fed into the solution prior to the inlet serves as a way to expedite the biofouling of the aqueous system and thus serves as an early warning mechanism since such expediting of the biofouling serves as a predictor of the biofouling which will occur in the overall aqueous system.

It is to be understood that both the forgoing general description and the following detailed description are exemplary and explanatory only and are intended to provide further explanation of the present invention, as claimed.

The accompanying drawings, which are incorporated in and constitute a part of this application, illustrates several embodiments of the present invention and together with the description, serve to explain the principles of some of the embodiments of the present invention.

DETAILED DESCRIPTION OF THE PRESENT INVENTION

Figure 1:
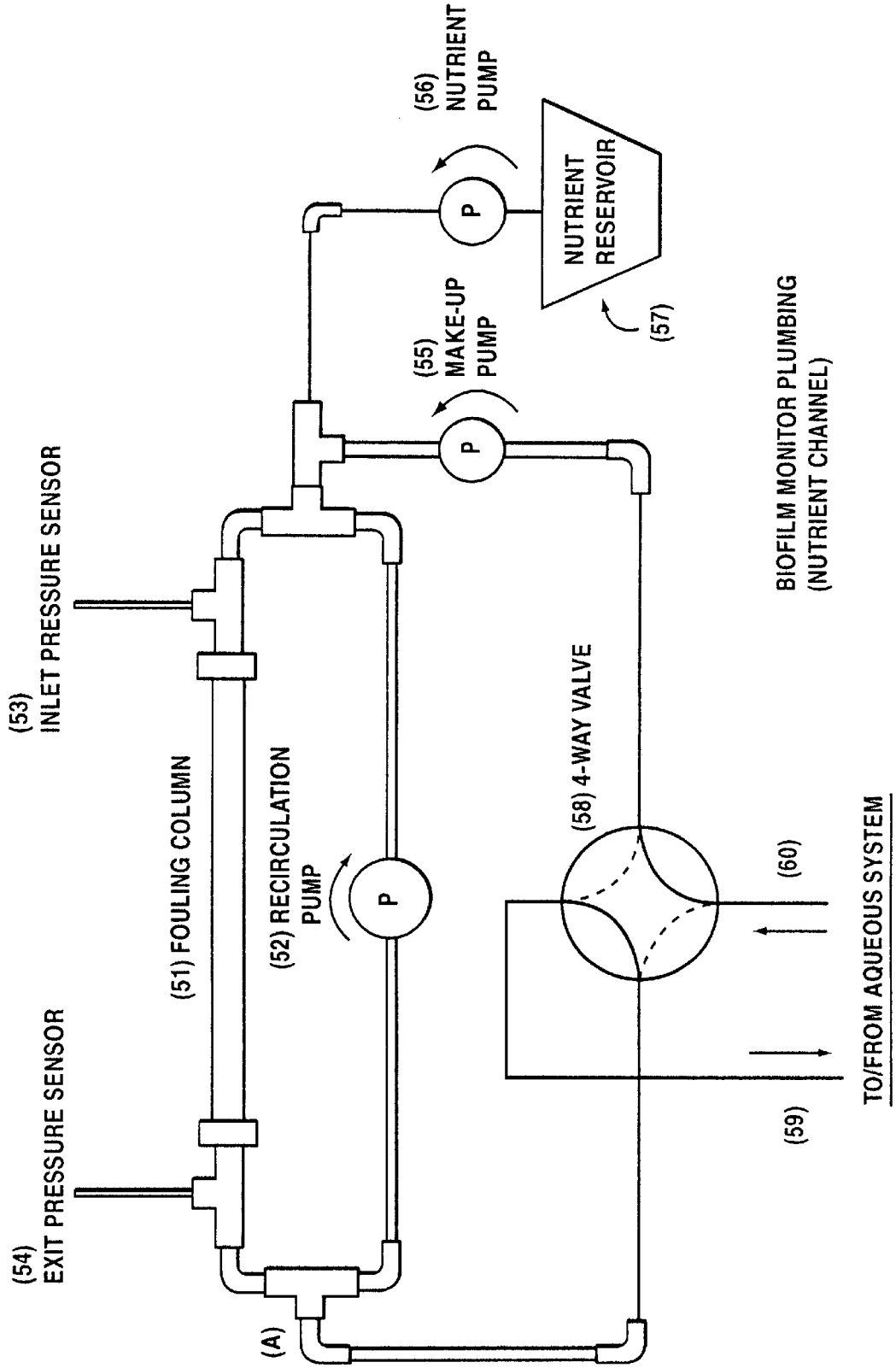
FIG. 1 is a schematic drawing of an embodiment of the biofouling monitor of the present invention.

The present invention relates to a biofouling monitor and a method to detect or monitor biofouling in an aqueous system such as a water system. For purposes of the present application, the aqueous or water system can be any such system including industrial water systems. Examples of water systems or aqueous systems include, but are not limited to, water systems used with paper making processes, cooling towers, and metal-working fluids. These various systems generally have surfaces which are susceptable to biofouling such as heat transfer surfaces, pipe lines, head boxes and paper making equipment, and liquid storage tanks and reaction vessels.

For purposes of the present invention, biofouling refers to fouling caused by biomass which is the buildup of microorganisms and/or extracellular substances and by dirt or debris that become trapped in the biomass. Bacteria, fungi, yeast, diatoms, protozoa, combinations thereof and other microorganisms are only some of the organisms which can cause build up of a biomass.

With respect to the biofouling monitor of the present invention, the biofouling monitor has at least a column having an inlet and an outlet. The monitor also has a microorganism nutrient feed line located upstream of the inlet of the column. Further, the biofouling monitor has a first pressure sensor which is located upstream of the inlet for measuring a first flow pressure and a second pressure sensor located downstream of the outlet of the column for measuring a second flow pressure.

The column having an inlet and an outlet can be any type of column which is hollow and permits the flow of an aqueous-type material through the interior of the column. The column can be any shape and size. For instance, the column can be circular, square, rectangular, triangular, or any other geometrical shape as long as it is hollow and permits the passing of aqueous-type material. Preferably, the column is circular. Further, the length of the column can be any length. For instance, the column can be from about 2 cm to about 200 cm. Preferably, the length of the column is from about 5 cm to about 100 cm, more preferably from about 5 cm to about 30 cm, and most preferably, from about 15 cm to about 25 cm. Also, the column can have any inner diameter or inner cross-sectional area. Preferably, this diameter or inner cross-sectional area is from about 0.1 $cm^2$ to about 100 $cm^2$, or more preferably from about 0.2 $cm^2$ to about 20 $cm^2$, and most preferably from about 1 $cm^2$ to about 3 $cm^2$. Ideally, the length and diameter or cross-sectional area is such to have a small pump maintain a pressure through the column and therefore larger diameters or cross-sectional areas and larger lengths of columns would require higher volumetric flow rates which are not preferred, if a self-contained mobile monitoring unit is preferred or needed.

The column can be made from any non-corrosive material such as plastic, glass, ceramic material like borosilicate glass beads, or a metal which is not corrosive such as stainless steel. Certainly, other non-corrosive materials can be used. Generally, the thickness of the wall of the column as measured by one-half the difference between the outer diameter and the inner diameter should be sufficient to avoid rupturing in view of the pressure of the liquid passing through the column. Preferably, this thickness should be from about 0.1 cm to about 1 cm and more preferably from about 0.2 cm to about 0.5 cm.

Generally, although it is not necessary, it is preferred that the column will have the same inner diameter or cross-sectional area throughout the column. Further, the inner diameter or cross-sectional area of the inlet and the outlet are preferably the same in order to maintain a uniform flow rate throughout the column.

With respect to the microorganism nutrient feed line, which is located upstream of the inlet of the column, any nutrient which promotes the growth of microorganisms can be used. For example, the microorganism nutrient feed can be a glucose formulation which contains water and glucose. Preferably, the glucose or other nutrient feed is present at a concentration of from about 0.5 ppm to about 1000 ppm, more preferably from about 5 ppm to about 500 ppm and most preferably from about 10 ppm to about 200 ppm. Other feed rates can certainly be used depending on the specific system being used. Generally, the microorganism nutrient feed is present in a holding tank wherein this nutrient feed is fed by a pump into the line containing the aqueous solution being fed into the inlet of the column.

The amount of microorganism nutrient feed which is introduced into the monitoring system is generally an amount sufficient to promote the growth of at least one microorganism in or on the surfaces of the column or any inert material that may be located in the column. The purpose of the microorganism nutrient feed is to create an optimal environment for growth of microorganisms on an expedited basis. By promoting such an expedited growth, biofouling will occur at a faster rate in the column compared to the overall biofouling rate occurring in the overall water system. By monitoring this expedited growth of microorganisms and therefore expedited microfouling, a prediction can be made with respect to the biofouling that will occur in the overall aqueous or water system subject to biofouling. Accordingly, the biofouling monitoring system of the present invention can be set up to have an early-warning system which can predict accurately the biofouling that should occur in the overall water system or aqueous system. If large amounts of microorganism nutrient are fed into the monitoring system, then biofouling will occur much faster in the monitoring system than in the overall aqueous system that is being monitored. If small amounts of microorganism nutrient are being fed into the monitoring system, then less advanced notice will be accomplished since the microfouling buildup will be only slightly faster than the overall biofouling buildup in the water system. For purposes of the present invention, each aqueous or water system being monitored will have a period of orientation to determine the type of advanced notice desired and a determination will also need to be made with respect to correlating the biofouling buildup in the column with the actual biofouling occurring in the aqueous system. Thus, when the biofouling monitor is used for the first time in an aqueous system, it is recommended that the aqueous system be cleaned or shutdown for biofouling removal and then when the aqueous system is restarted the biofouling monitor can obtain an accurate reading of the biofouling occurring in the aqueous system versus the biofouling buildup in the monitoring system. Once the correlation is determined between the actual biofouling occurring in the aqueous system and the advanced biofouling occurring in the column, the user of the monitoring system can then appreciate the type of advance notice being provided by the monitoring system and a decision can be made whether to increase the advanced notice or to decrease the advanced notice based on the amount of microorganism nutrient being fed into the column. Other factors that can control the amount of biofouling occurring in the column are the size and shape of the packing material, the recirculation flow rate through the column, and the amount of aqueous solution from the aqueous system being entered from the uptake valve. In other words, if a recirculation system is being used, the finer the packing material or the more recirculation of the existing aqueous solution in the monitoring system, or the more aqueous solution being introduced from the aqueous system, the faster the response to biofouling buildup.

With respect to the pressure sensors, at least two pressure sensors are located in the monitoring system. The first pressure sensor is located at the inlet of the column to monitor the pressure of the aqueous solution entering the column and a second pressure sensor is located at the outlet or near the outlet of the column to monitor the pressure of the aqueous solution exiting the column. These two pressure readings can then be compared to monitor any pressure drop occurring. By monitoring the pressure difference between the two sensors, and plotting these measurements, a pattern of changing pressure differentials can be seen which represents biofouling buildup. In other words, as the difference in pressure increases, the biofouling buildup is increasing in the column since the biofouling buildup is increasing the resistance to flow of the aqueous solution through the column and thus is increasing the pressure at the inlet to the column relative to the column exit. By monitoring the pressure differential based on these pressure sensor readings, a clear understanding of the biofouling buildup in the overall aqueous system can be seen. The pressure sensors that can be used in the present invention can be any pressure sensor capable of recording water flow pressures such as electromechanical transducers.

Typically, the pressure of the aqueous solution entering the inlet of the column can be any pressure which can be adjustable by using at least one pump in the monitoring system. Typically, the pressure, if a recirculation system is not used will be from about 0.1 mbar to about 1000 mbar and more preferably from about 1 mbar to about 100 mbar. Other pressure rates can certainly be used depending upon the specific aqueous system being monitoring.

In a preferred embodiment of the present invention, a recirculation system is used. The recirculation system essentially recirculates the aqueous solution passing through the column. This recirculation system has at least two purposes. First, the recirculation system permits an increase and sustained higher pressure of the aqueous solution through the column which can be adjustable depending upon the need of the specific monitoring system. The second purpose of the recirculation system, as mentioned above, is to recirculate the aqueous solution through the column thereby avoiding the introduction of large volumes of fresh aqueous solution from the overall aqueous system that would otherwise be needed to sustain the necessary pressure. The introduction of large volumes of fresh aqueous solution introduces suspended debris that can clog the column and in addition, can flush microorganisms out of the column before they can multiply and cause the biofouling. Typically, the recirculation system will have an entry point prior to the inlet of the column and upstream of the microorganism nutrient feed line and will have an exiting point after the outlet of the column. As indicated, the recirculation system can create any type of water pressure across the column such as from about 0.1 mbar to bout 1000 mbar, more preferably from about 0.5 mbar to about 200 mbar, and most preferably from about 1mbar to about 100 mbar. Any pump that can sustain such pressures can be used such as a peristaltic pump. Further, even though a recirculation system is being used, the overall monitoring system still permits the exiting of at least a portion of the aqueous solution which exits from the outlet of the column. This exiting of at least a portion of the aqueous solution will permit the introduction of fresh aqueous solution from the overall aqueous system in order to maintain an accurate representation of the water flowing through the overall aqueous system to provide a more accurate biofouling indication. The amount of the aqueous solution which exits the overall monitoring system into a holding tank or downstream of the intake point is from about 0.1 to about 2000 ml/min. Accordingly, the introduction of fresh aqueous solution into the monitoring system occurs with the use of a make-up line which pumps additional aqueous solution into the monitoring system at a point before or after the recirculation entry point. The amount of the fresh aqueous solution being entered into the monitoring system having a recirculation system can be any amount such as from about 0.1 ml/min to about 2000 ml/min, more preferably from about 0.5 ml/min, to about 10 ml/min, and most preferably from about 1 ml/min to about 3 ml/min.

Another option of the present invention which is preferred, is including inert packing material within the column. The amount of this inert packing material should not exceed an amount which will prevent the passing of any liquid containing material through the column. While any inert packing material can be used, examples included, but are not limited to, rocks, glass, non-corrosive metal, ceramic material, or a combination thereof. A preferred inert packing material is at least one stainless steel ball. The amount of inert packing material is dependent on the size of the interior of the column as well as the amount of surface area the user desires to create an environment for biofouling buildup.

FIG. 1 shows a schematic of one embodiment of the present invention. In this Figure, a fouling column 51 is located between an inlet pressure sensor 53 and an exit pressure sensor 54. A recirculation pump 52 is located such that an aqueous solution containing microorganism nutrients is recirculated through the column 51. A make-up pump 55 pumps in fresh aqueous solution from the aqueous system (via the inlet 60) to be introduced with the recirculated aqueous solution as shown in FIG. 1. A nutrient pump 56 pumps in microorganism nutrient from the nutrient reservoir 57, and this nutrient enters into the column as shown in FIG. 1. An amount of used aqueous solution containing nutrients exits the column system at point A and re-enters the aqueous system at a point downstream of the inlet, via the outlet stream 59. A four-way valve 58 can be used as shown in FIG. 1 to permit a by-passing network should one be needed.

Another embodiment of the present invention involves a second biofouling monitoring system which can run in parallel with the first monitoring system. Thus, a second column having an inlet and an outlet with an optional microorganism nutrient feed line located upstream of the inlet of the second column can be used. This second column like the first column described above will also have at least two pressure sensors and optionally a second recirculation system. Also, inert packing material can be included inside the column. This second biofouling monitoring system can serve a variety of purposes. First, the biofouling monitoring system can simply be a control which merely passes aqueous solution from the aqueous system through the column without any micronutrient being feed. Alternatively, the second monitoring system can be used as a check on the first monitoring system to obtain an accurate average of the advanced biofouling that is occurring should nutrient feed lines be used in both monitoring systems.

Figure 2:
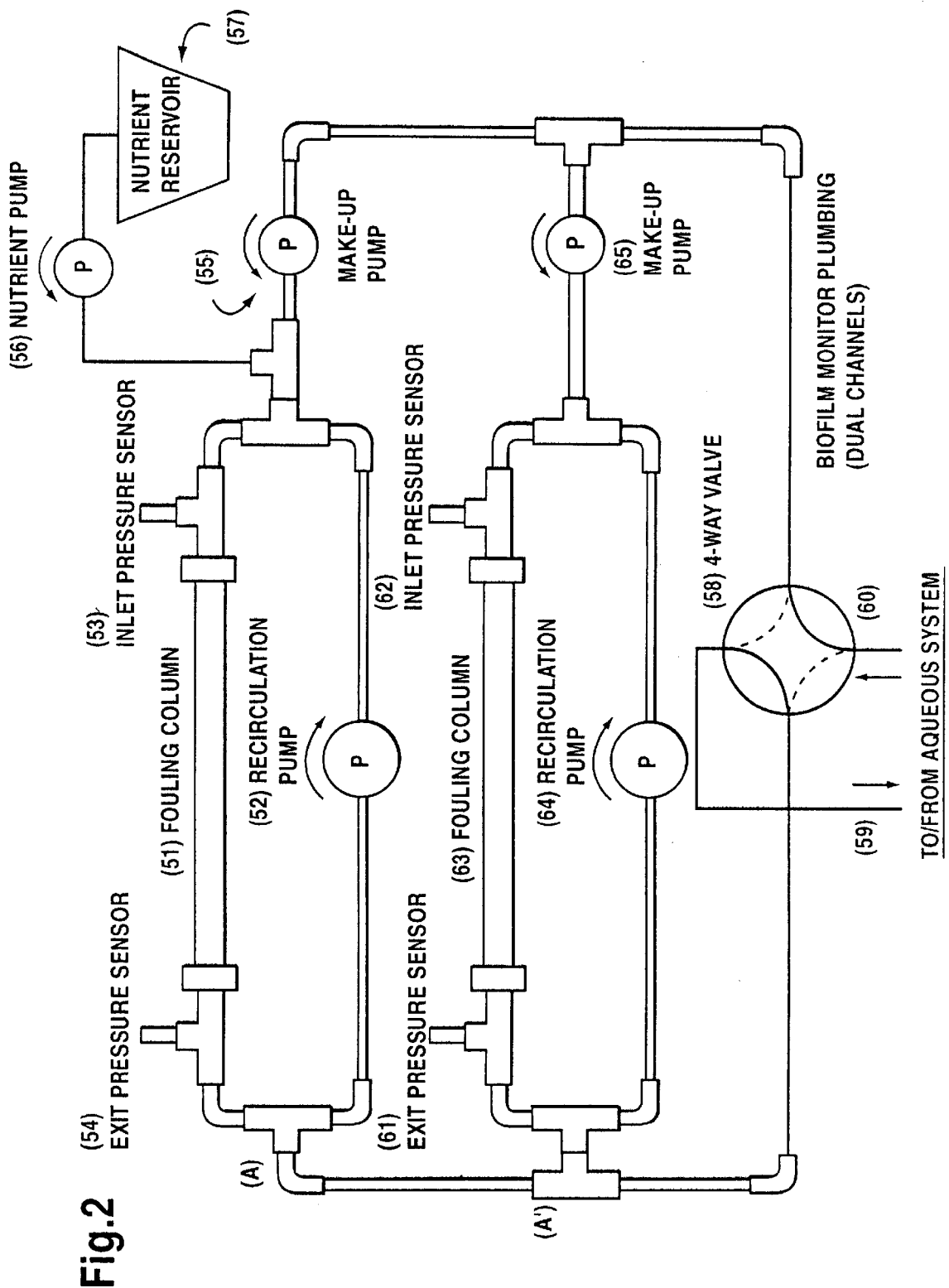
FIG. 2 is a schematic drawing of another embodiment of the biofouling monitor of the present invention.

FIG. 2 shows an embodiment of a two column system. The first column and its hook-up is the same as described with respect to FIG. 1 and the numerals depict the same parts and their location. In addition to this hook-up, as shown in FIG. 2, a second column 63 is located between an inlet pressure sensor 62 and an exit pressure sensor 61. A second recirculation pump 64 is located as shown in FIG. 2 to recirculated aqueous solution which can optionally contain nutrients or can simple recirculate the same amount of aqueous solution as recirculation pump 52 in order to maintain an accurate control. A make-up pump 65 is located to introduce fresh aqueous solution. A and A' represent the points where the aqueous solution exits the column systems to be re-introduced into the aqueous system as described above.

In view of the above, the present invention further relates to a method of monitoring or detecting biofouling ahead of time in an aqueous system. This method involves the use of one or more biofouling monitoring systems as described above. In more detail, the method to monitor or detect biofouling ahead of time involves passing at least a portion of the aqueous solution on a continuous basis through a column having an inlet and an outlet. The method further involves introducing a microorganism nutrient into the aqueous solution to be passed through the column at a point upstream of the inlet of the column. The method also involves measuring flow pressures through the column at the inlet and at the outlet on a continuous or non-continuous basis. The pressure differential based on these measurements can then be determined and a correlation can be made to determine the advance biofouling that will occur in the overall aqueous system.

To further provide an environment to optimize the biofouling buildup in the column, heating units can be used to maintain a temperature of the aqueous solution passing though the column at a temperature sufficient to promote the growth of microorganisms. Typically, the temperature of the aqueous solution passing through the column is preferably from about 80° F. to about 140° F., and more preferably from about 90° F. to about 100° F. The heating units used can be any heating unit capable of maintaining a desired temperature of aqueous solutions. Such units include but are not limited to heating tapes or mantles.

For purposes of the present invention, the various parts of the biofouling monitor of the present invention can be connected with each other by any type of piping network such as flexible or rigid PVC tubing or other conventional piping. The manner of hooking up the various parts of the present invention with the piping network is the same as any hook-up of a piping network.

Figure 7:
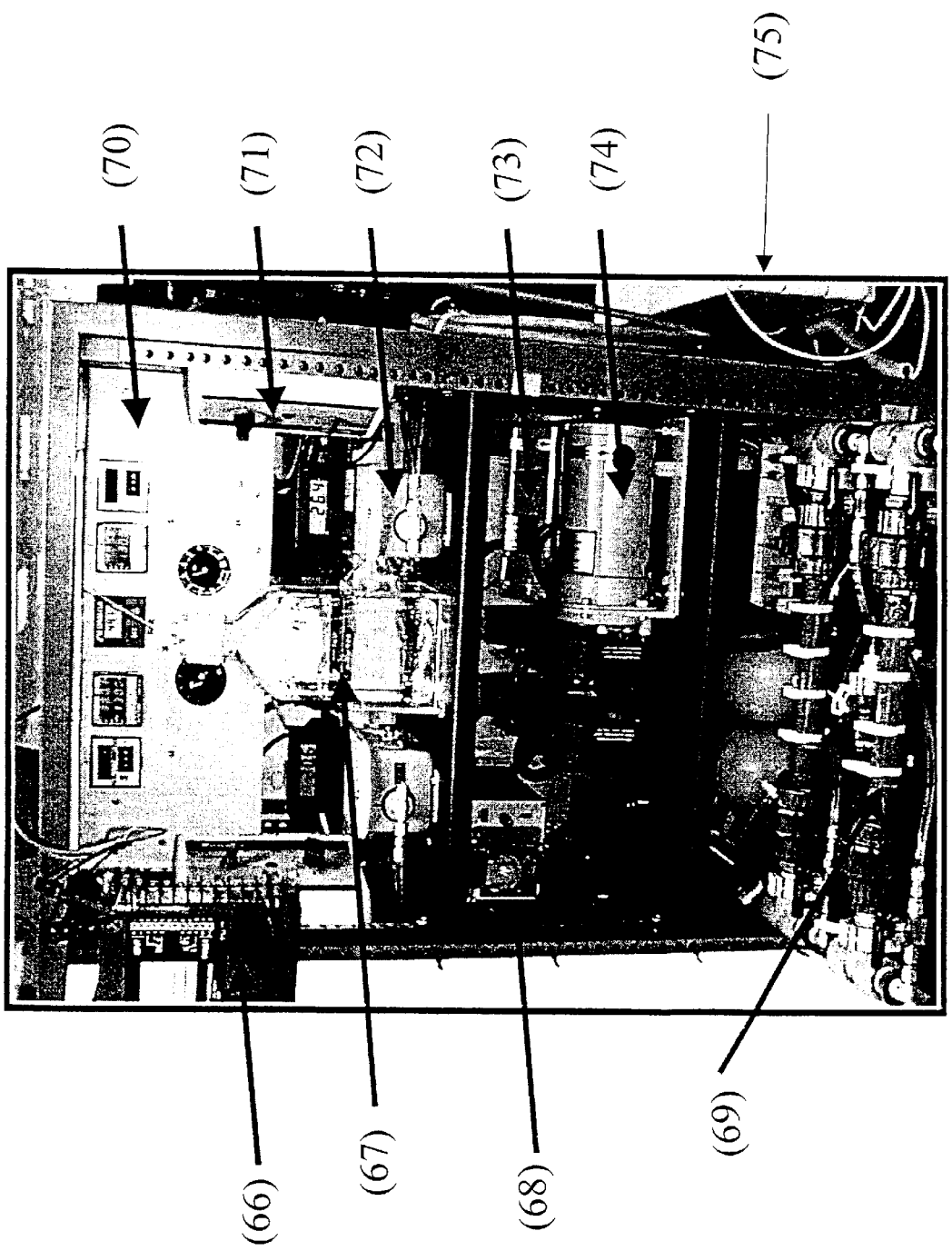
FIG. 7 is a photograph of an embodiment of a self-contained biofouling monitor of the present invention.

An advantage of the present invention is that the biofouling monitor can be a self contained unit which is extremely mobile and thus can be taken to various sites to monitor biofouling buildup. FIG. 7 shows a depiction of such a self contained monitoring unit which in this embodiment has a size of 22"w×18"d×30"h and weighs about 100 lbs. As shown in FIG. 7, a self-contained biofouling monitoring unit 75 is shown. The unit 75 has data loggers 66, a nutrient reservoir 67, a nutrient feed pump 68, one or two fouling columns 69 (two are shown though one could be used alone), temperature control panel 70 for controlling the temperature of the aqueous solution passing through the column(s), pump speed controllers 71, pressure gauges 72, make-up pump 73, and a recirculation pump 74.

With respect to the use and advantages of introducing at least one microorganism nutrient into a biofouling monitor system, another embodiment of the present invention relates to a method to detect biofouling ahead of time or on an expedited basis. The method involves at least the step of introducing at least one microorganism nutrient as described above into at least a portion of an aqueous solution which is passing through a biofouling monitor system. Typically, the microorganism nutrient will be introduced prior to a point wherein any monitoring of any biofouling is occurring. Also, preferably the aqueous solution in which the at least one microorganism nutrient is being introduced will have a sufficient environment for the growth of microorganisms to promote biofouling. The biofouling monitor system which is useful for this embodiment can be any biofouling monitor system.

Another embodiment of the present invention relates to a method to expedite the biofouling rate occurring in a biofouling monitor system which involves introducing at least one microorganism nutrient as described above, into a test sample. The test sample is typically a sample of the aqueous solution or aqueous sample which is used in the residential, commercial, or industrial aqueous process and water handling systems. The amount of microorganism nutrient that is introduced can be of any amount, and preferably is an amount which promotes an expedited growth of microorganisms compared to the aqueous or water system which is being tested. The amounts of microorganism nutrient can be determined based on the particular aqueous or water system being monitored for biofouling.

The present invention will be further clarified by the following examples, which are intended to be purely exemplary of the present invention.

EXAMPLES

Fluid flow through porous media generates a pressure differential due to viscous interaction between the moving fluid and the surface of the media. As the surface area for viscous interaction increases, frictional resistance and differential pressure increase. The magnitude of the pressure differential is effected by fluid density, viscosity, flow rate, porosity, and the roughness of the media surface ($C_m$) according to Darcy's Law:

$$\text{Pressure} = C_m \times [\text{viscosity}/(\text{density} + \text{porosity})] \times \text{flow rate} \quad (\text{eq. 1})$$

Surface deposits such as microbial cells and the associated debris found in biofilms can increase the media roughness resulting in an increase in pressure. Pressure is further increased as the deposits begin to significantly occlude the fluid flow path, causing a decrease in porosity. These effects are commonly encountered in porous media filtration where biofouling can significantly degrade filter performance, yet here the same principals form the basis of a sensitive detector to monitor biological fouling.

In this example, a differential pressure biofouling monitor was made in which a packed column of metal beads provides a large surface area for fouling to create a sensitive, reliable instrument. The instrument eliminated the need for high flow velocities to achieve a measurable signal.

A challenge in using packed column technology to monitor biofouling is the tendency or non-biological material and debris to clog the column and interfere with the biological signal. This is particularly true in paper mill white water circuits where large amounts of suspended material are present. The invention employs design features to avoid this problem and incorporates technology to discriminate biological from non-biological fouling.

The ability of the biofouling monitor to handle high levels of suspended solids is achieved by using a recirculation pump to generate rapid flow through the column while using a separate make-up pump to introduce fresh process water into the system at a slower rate. This approach maintains a continuous supply of process water without the need to pump large volumes of fresh solution with attendant solids through the system. The small volume of process water can be readily filtered upstream of the biofouling monitor permitting high solids sources such as short-loop white water to be used with the instrument. The retention time of fluid in the. system can be adjusted using the make-up pump thereby providing one of several means to adjust the sensitivity of the instrument.

Instrument sensitivity is of key importance in correlating the response of a biofouling monitor with the performance of the industrial process being monitored. In almost all cases, the purpose of the monitor is to detect slime deposits before they reach a level that degrades product quality. To do so, the monitor should generate a measurable signal in advance of damaging build-up. The current device incorporates several means to control the rate of biofouling in the instrument enabling the instrument response to be readily correlated with process quality.

The device allows the rate of process water feed to be adjusted to increase or decrease the supply of fresh solution to the monitor. This in turn influences the microbial growth rate by increasing or decreasing the supply of nutrients available for growth. A. second means to control instrument sensitivity is by adjusting the recirculation flow rate. Higher flow rates amplify the pressure changes caused by changes in media roughness, fluid viscosity, density, and porosity according to eq. 1. The size and shape of the material used to pack the columns can also be used to adjust sensitivity. As an example, columns packed with small diameter beads will respond quickly to biofouling since little deposit is needed to occlude the voids between the beads (i.e. the porosity decreases quickly as fouling develops).

The above adjustments can all be used to modify the sensitivity of the monitor, however experience has shown that long periods of slime free paper machine operation are often followed by abrupt increases in fouling that begin to degrade paper quality in as little as a few days. It is highly desirable to have an advance warning of such slime build-up which would allow the operator to increase microbicide dosage or arrange for a timely shutdown for preemptive cleanup. In this example, the present device incorporates two channels, one of which uses a supplemental nutrient feed pump to introduce nutrients that accelerate microbial growth in that channel. Using this approach, the nutrient enriched channel gives a several day advance warning of biofouling compared to the channel supplied with process water only. It is an advantage of the design that acceleration of the fouling signal by nutrient addition confirms that the fouling is at least partly biological in nature since abiotic fouling would show no response to the addition of microbial nutrients.

INSTRUMENTATION

The biofouling monitor in this example was a stand-alone system designed to monitor slime and deposit build-up in paper machine and other industrial water circuits. The system comprised multiple pumps, pressure transducers, temperature controllers, and data loggers housed in a 18"d×22"w×30"h metal cabinet. An intake peristaltic pump (Cole-Parmer Instrument Company model E-07553-80) in the monitor cabinet delivered water from the industrial process at 2–3 ml/min into dual 1.5 cm inside diameter×20 cm long clear PVC columns filled with 1.5 mm diameter 302 stainless steel beads that served as a substratum for biofilm attachment. A separate peristaltic pump recirculated water through the columns at 250 ml/min to generate a baseline pressure drop between 20 and 30 mbar. Glucose (30,000 ppm) was fed at approximately 50 ul/min from a 1 liter reservoir to the second of the two channels (channel 2) by a separate pump (Cole Parmer model E-7710-30) producing an approximately 600 ppm glucose addition to stimulate microbial growth. The bead columns were cemented to PVC quick connect unions for easy replacement and the entire biofouling monitor liquid flow path comprises PVC and stainless steel fittings and chemically resistant Norprene and Tygon tubing to allow cleaning solution to be pumped through the system for cleanup. The bead columns were heated with electric mantles (Cole Parmer model E-03125-20) using Omega CN76000 temperature controllers to maintain a desirable temperature such as 100° F. to stimulate microbial growth. Omega CN375 thermal limit controllers monitored the surface temperature between the heating mantle and the clear PVC bead columns to prevent melting of the PVC. Differential pressure gauges (Cole Parmer model E-07354-05) with 4–20 mA output signals were attached with ⅛" id×¼" of water filled tygon tubing to PVC 'tee' fittings located at either end of the columns. The pressure gauges measured differential pressure across the bead filled columns and displayed the data on digital and bar graph meters (Cole Parmer model E-94712-00) located on the cabinet front panel. The 4–20 mA output from the pressure gauges was passed through a 100 ohm resistor to produce a 0.4–2 Vdc signal proportional to pressure, that was read at 10 minute intervals by an Onset Computer HOBO 8 data logger located within the cabinet. The entire biofouling unit was self-contained and required only 120 Vac single phase electrical power and a continuous source of process water for operation.

To initiate a monitoring period, clean columns were installed into the biofouling monitor and process water was pumped into the system with the make-up pump; the recirculation pump and nutrient feed pump were started, and the data loggers were launched. In many applications, a baseline period will ensue during which pressure remains constant followed by a rapid—typically exponential—increase in pressure. The baseline and exponential periods denoted the induction and growth phases respectively.

The biofouling monitor was experimentally deployed at a Kraft pulp, alkaline fine paper mill to evaluate the instrument performance and to examine the effect of supplemental nutrients on the fouling response. The mill chosen produced 600–1000 tons per day of coated fine paper on a single machine using a mixture of hardwood, pine, and broke from an off-line coater. Slime formation at the mill was kept under good control using a combination of halogen and organo-bromine biocides, however pressure to decrease biocide dosage made the mill an excellent site for the monitor trial. During the initial tests described here, a baseline fouling response was established against which future efforts to reduce biocide usage can be compared.

Solution for the biofouling tests was drawn from clarified white water that had passed an Albany screen. The water was additionally processed through a small clarifier and a 20 $\mu$m filter to further lower suspended solids prior to entering the biofouling monitor. These steps minimized fouling from suspended material to allow the response to biological fouling to be evaluated. In normal operation, rapid solution turnover in the clarifier ensured that stagnant growth conditions were avoided. Make-up to the biofouling unit was continuous at 2–3 ml/min giving a residence time of approximately two hours within the recirculation loop. Temperature of the influent solution was 12–0130° F. Supplemental glucose was fed to the second of the two biofouling channels to give a final solution concentration of 600 ppm.

Figure 3:
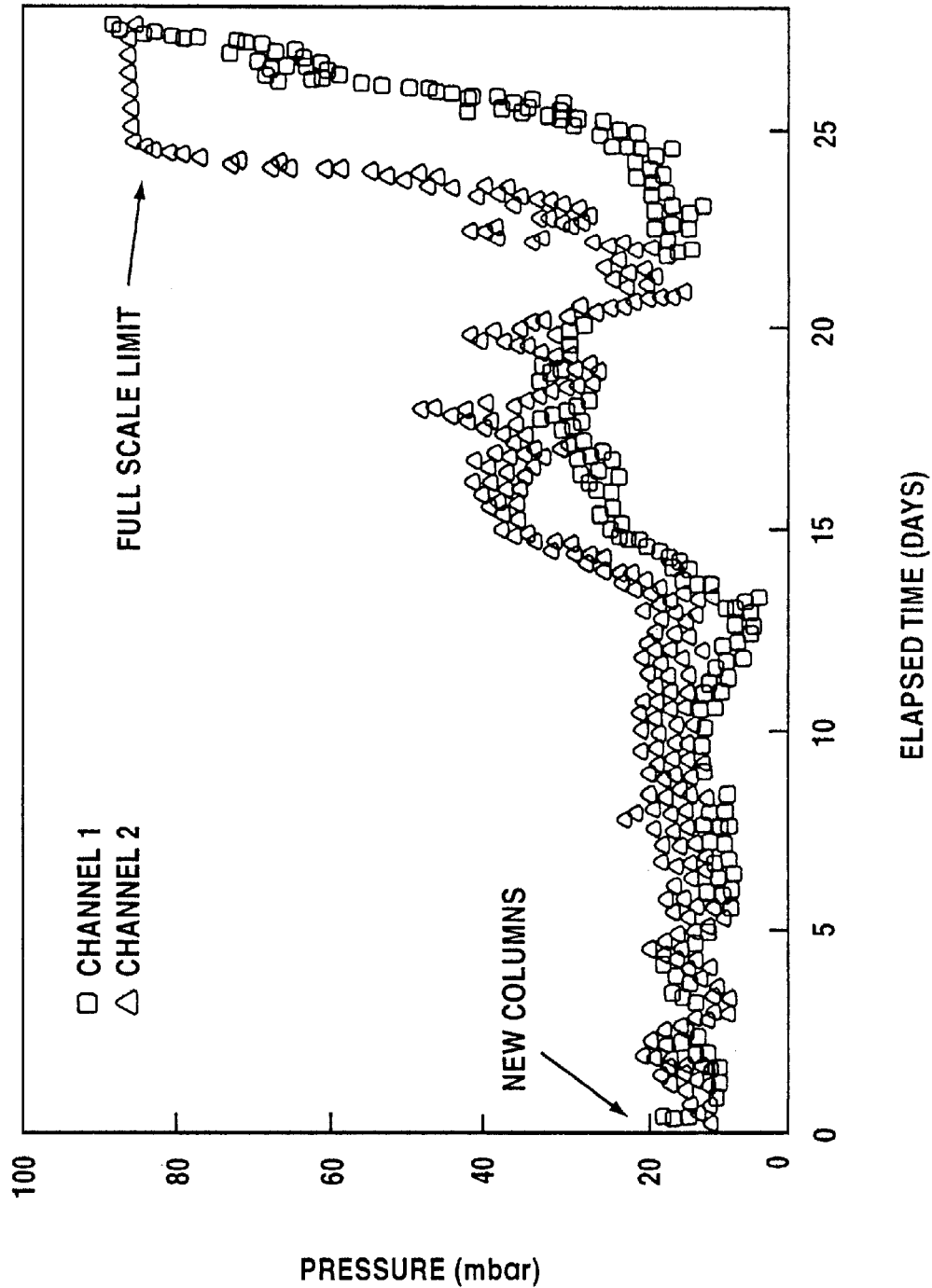
FIGS. 3–6 are graphs depicting the recordation of pressure over time from the Example, showing a biofouling buildup which serves as an early prediction for biofouling which will occur throughout the overall aqueous system.
Figure 4:
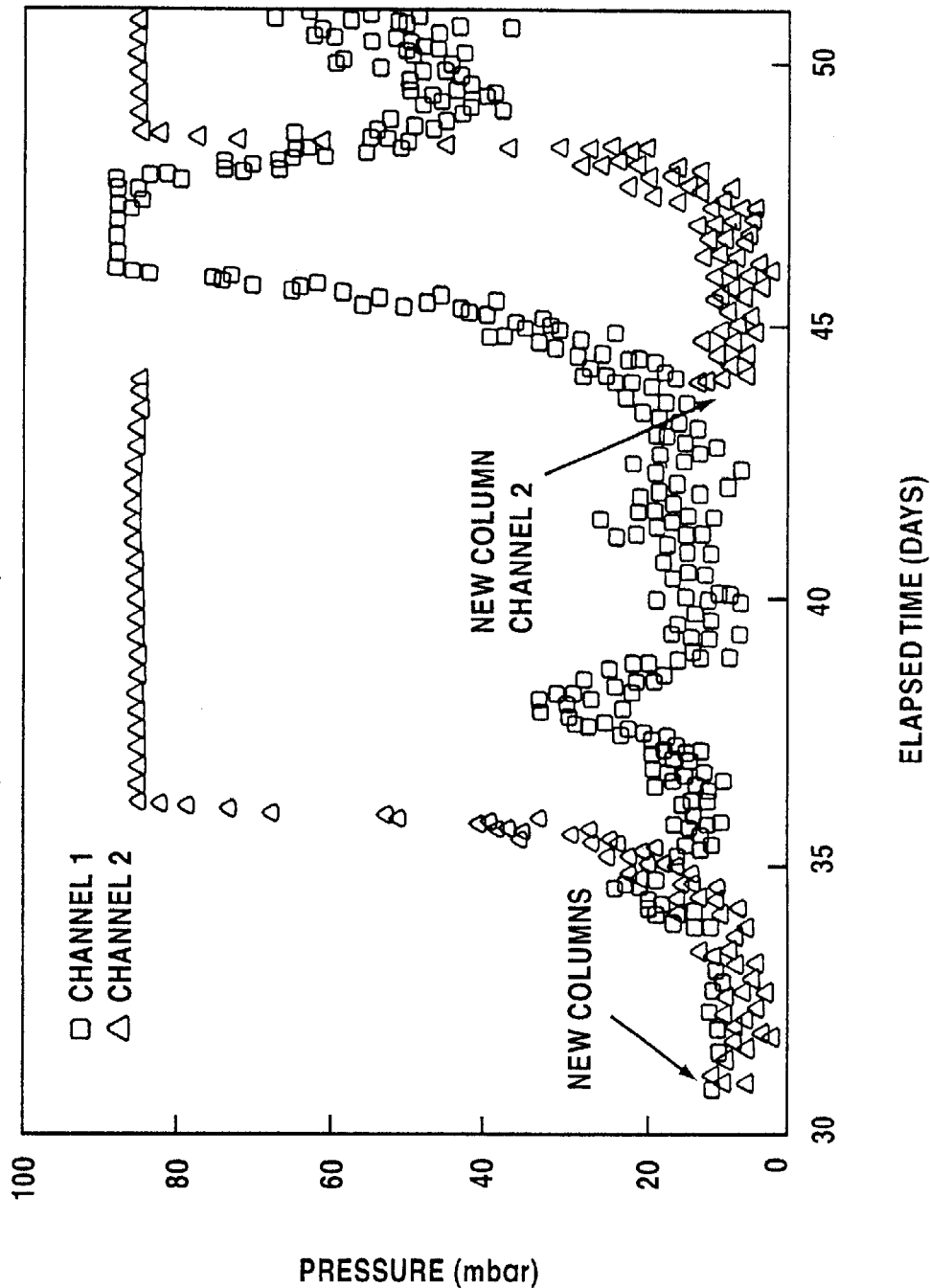

The monitor, outfitted with clean fouling columns, was placed on-line concurrently with the paper machine startup at completion of a wet-end boilout. This timing allowed the fouling response to be referenced to a clean machine state. After 31 days, the fouling columns for both channels were replaced and after 44 days the column for channel two was again replaced. The paper machine wet-end was boiled out at day 38 during a scheduled maintenance operation. FIGS. 3 and 4 show the data record for the 51 day deployment.

The fouled columns removed at day 31 were visually examined for the presence of slime by removing the stainless steel beads and examining the bead surface with a hand lens at 10×. The beads were also analyzed for microbiological activity by extracting the deposits with surfactant and analyzing the extract using a commercial ATP analyzer. Separate samples of the deposits were removed by ultrasonification and examined for elemental content using energy-dispersive x-ray fluorescence analysis.

Results

The data record showed an initial fourteen day period during which the signals for both channels remained stable at 10–20 mbar. Between day fourteen and day twenty, an excursion to 30 to 40 mbar and a subsequent return to baseline occurred for both channels. At day twenty one, the signal for the glucose channel (channel 2) began to increase exponentially to a limiting value of 80 mbar corresponding to the maximum signal for the pressure transducers. Two to three days later, the signal for channel one showed a similar exponential increase. Clean new fouling columns were installed at day 31 causing the signals to return to a low baseline level.

The next fouling event for channel two occurred three to four days after the new columns were installed, and was again followed approximately three days later by what appears to be the start of an exponential shift for channel one. The later increase was truncated when the paper machine was boiled out at day 38, then recurred after six to seven days reaching a limiting value at day 46. A few days later, the signal for channel one dropped to approximately 50 mbar. A new fouling column installed on channel two at day 44 resulted in a response very similar to the behavior at days 32–36.

Visual examination of deposits on the stainless steel beads was made at day 31 prior to installing new columns. Pale yellow to amber slime streamers within the columns were visible by eye and examination of the deposits at 10× showed a web-like matrix of biofilm spanning the voids between beads. ATP analysis showed the presence of heavy microbiological activity in material extracted from the bead surface. Elemental analysis of the deposits showed peaks for aluminum, silica, and calcium, indicating that clay and calcium carbonate fines were also present in the material.

The appearance of a baseline region on installation of new columns corresponded to the period of slow, initial microbial attachment (the induction period) often observed in biofouling. The similarity in baseline data for the two channels indicated both respond uniformly to small fluctuations in signal that may have been caused by variations in suspended solids and fines that enter the system. Such material will alter the viscosity and density of the solution and by Darcy's Law will effect pressure drop across the fouling columns. The data record showed these fluctuations were quite easily distinguished from true fouling events.

The pressure excursion beginning at day 14 is not clearly explained, however the event coincided with formation of a clogged line that stopped flow to the clarifier. The signal increases at day 22 for channel two and day 25 for channel one illustrated the two to three day advance warning given by the glucose channel. This result is consistent with the increase in induction time expected for the higher nutrient concentration. Comparing the signals for channels one and two after installing new columns (day 31) again showed the glucose channel to give a two to three day advance warning of biofouling (here the response for channel one is truncated by the paper machine boilout).

Installation of new fouling columns in channel two (days 32 and 44) resulted in an exponential increase similar to the one described above but which began much sooner. In both cases, the more rapid increase started 3–4 days after the columns were installed and may have been promoted by an inoculum of microorganisms within the monitor that was not cleaned out when the fouling columns were replaced. The decrease in signal for channel one at day 38 coincides with the wet-end boilout and further illustrates the instruments response to factors influencing microbial growth. The drop in signal for channel one at day 47 may be an incident of sloughing in which pressure changes as part of the slime layer detaches or shifts within the fouling column.

Figure 5:
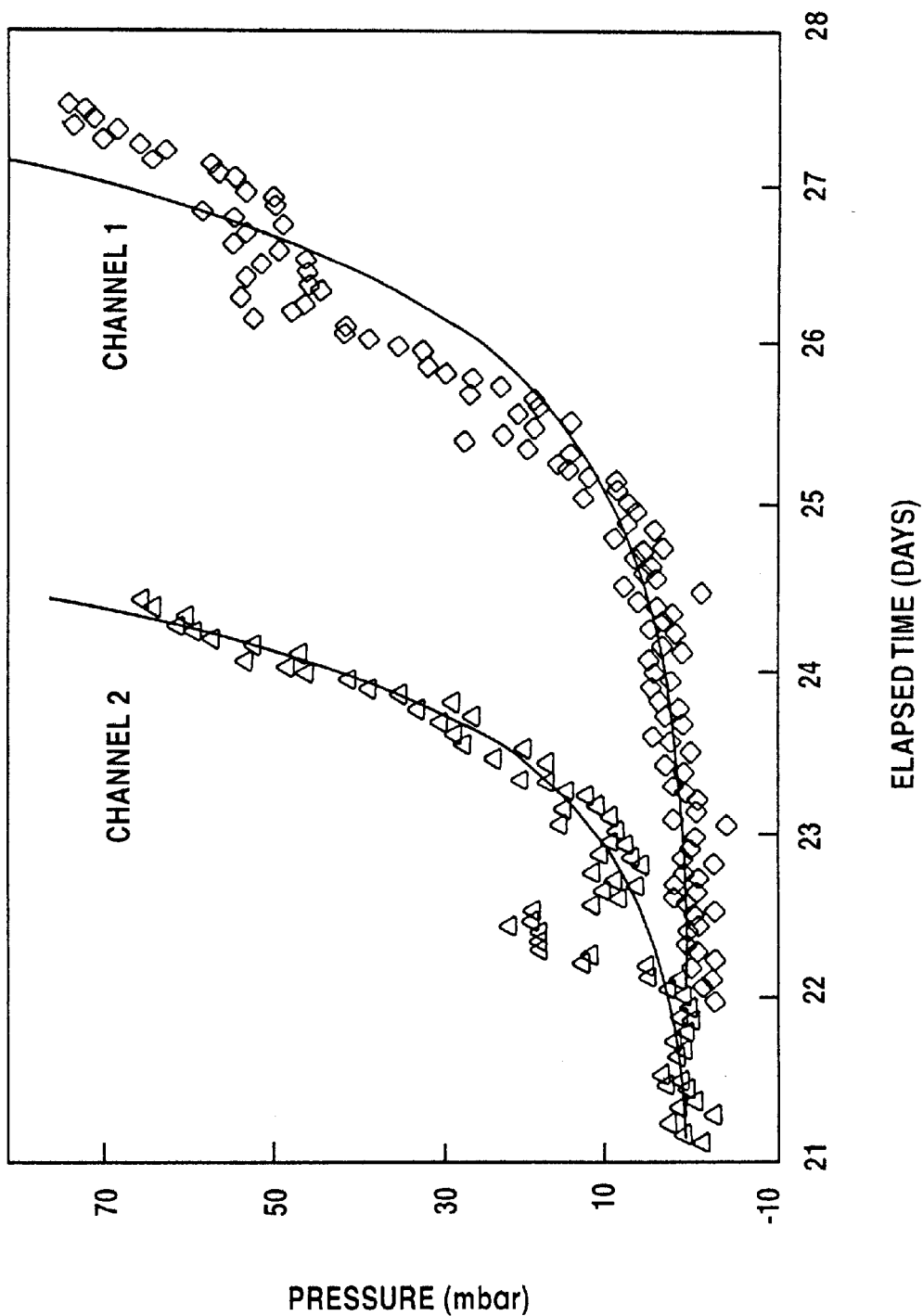
Figure 6:
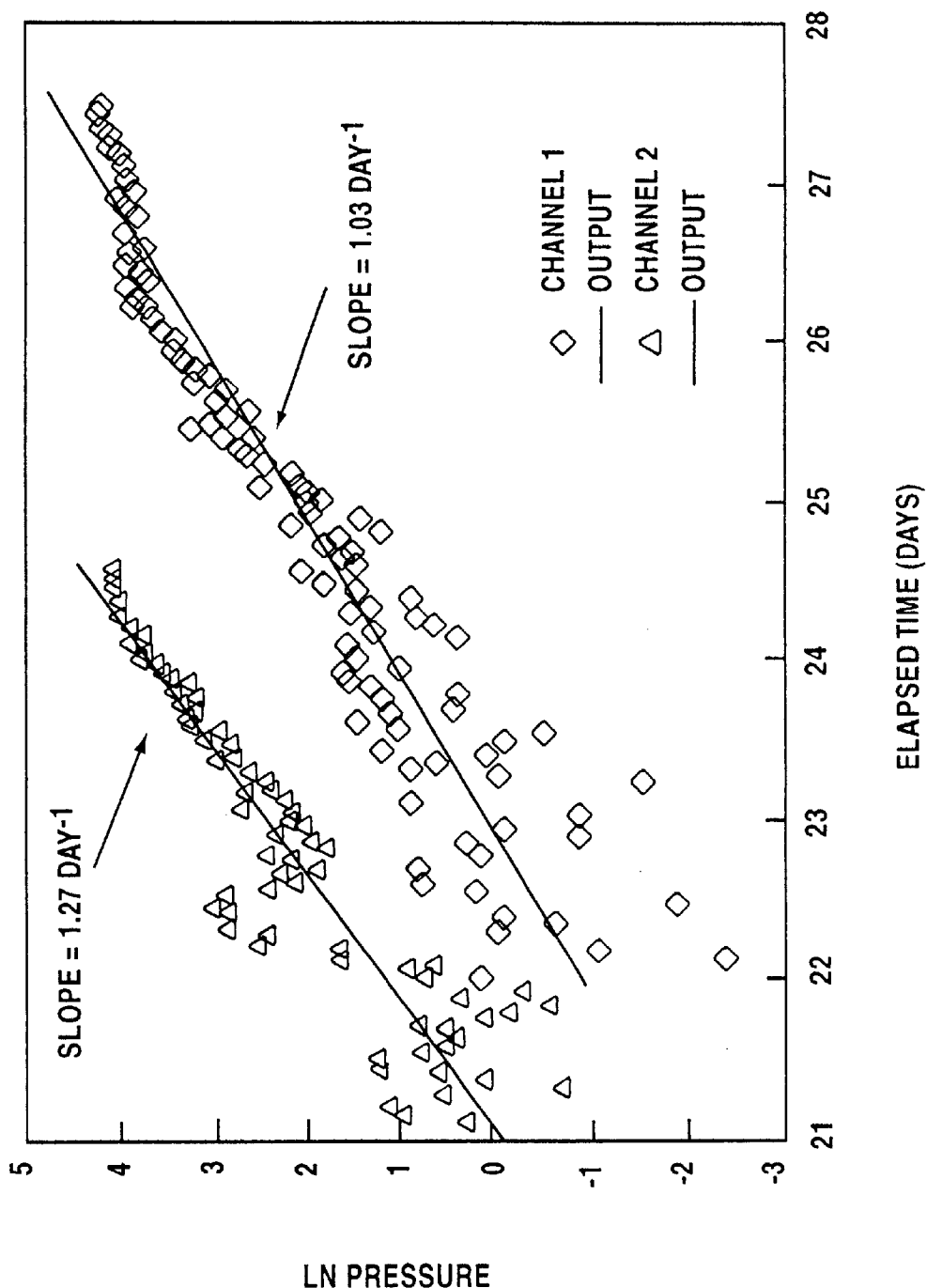

The exponential form of the fouling signal at day 22 and day 25 is consistent with biological fouling and further illustrates the effect of glucose addition on the instrument response. FIG. 5 shows an exponential curve fit to data in these regions and FIG. 6 shows a plot of the logarithm of pressure versus time. The slope of the later curves gives a specific fouling rate of 1.03 $d^{-1}$ and 1.27 $d^{-1}$ for channels one and two respectively. These values correspond to 16 and 13 hours respectively as the time required for the fouling signal to double. Analysis of the fouling signals at day 36 (channel 2) and day 45 (channel one) also shows a higher specific fouling rate for the glucose channel.

The paper mill evaluation demonstrates that microbial activity and slime formation in paper mill white water can be measured using the on-line monitor. ATP and elemental analysis indicate that the fouling deposits comprise both microbial and inorganic materials as is typical of the slime and trapped debris found in paper machine deposits. The wet end chemistry of paper produced during the monitor evaluation did not show slime related problems indicating that the monitor is able to discern microbial activity before it begins to degrade paper quality. The response to microbial activity is accelerated by supplemental nutrient addition which provides an advanced warning of the biofouling. Under normal operation, the signal on the nutrient augmented channel can be used to predict that fouling will occur in a few days time, giving mill operators the opportunity to supplement the biocide addition, for example to extend production through a crucial product run, or to arrange a timely shut down for preemptive cleanup.

Other embodiments will be apparent to those skilled in the art from consideration of the present application and practice of the present invention disclosed herein. It is intended that the specification and examples be considered as exemplary only, with the true scope and spirit of the invention being indicated by the following claims.

What is claimed is:

1. A biofouling monitor comprising:
   a) a column having an inlet and an outlet;
   b) a microorganism nutrient feed line located upstream of said inlet;
   c) a first pressure sensor located upstream of said inlet for measuring flow pressure and a second pressure sensor located downstream of said outlet for measuring flow pressure; and
   d) optionally, a heating system on the column; and
   further comprising an inert packing material located within said column and in an amount to permit the passing of a liquid containing material through said column.

2. The biofouling monitor of claim 1, wherein said column is a column made from plastic, glass, a ceramic material, or a metal.

3. The biofouling monitor of claim 1, wherein said microorganism nutrient feed line contains a glucose, pyruvate, or starch formulation.

4. The biofouling monitor of claim 1, wherein said inert packing material comprises rocks, glass, plastic, non-corrosive metal, ceramic material, or combinations thereof.

5. The biofouling monitor of claim 1, wherein said inert packing material is at least one stainless steel ball.

6. A biofouling monitor comprising:
   a) a column having an inlet and an outlet;
   b) a microorganism nutrient feed line located upstream of said inlet;
   c) a first pressure sensor located upstream of said inlet for measuring flow pressure and a second pressure sensor located downstream of said outlet for measuring said flow pressure;
   d) a re-circulation system connected to the inlet downstream of said feed line, and connected to the outlet for maintaining a pressure feed through said column;
   e) inert packing material located in said column in an amount to permit the passing of a liquid containing material; and
   f) optionally, a heating system located on said column.

7. The biofouling monitor of claim 6, wherein said column is a column made from plastic, glass, a ceramic material, or a metal.

8. The biofouling monitor of claim 6, wherein said microorganism nutrient feed line contains a glucose, pyruvate or starch formulation.

9. The biofouling monitor of claim 6, further comprising an inert packing material located within said column and in an amount to permit the passing of a liquid containing material through said column.

10. The biofouling monitor of claim 6, wherein said inert packing material comprises rocks, glass, plastic, non-corrosive metal, ceramic material, or combinations thereof.

11. The biofouling monitor of claim 6, wherein said inert packing material is at least one stainless steel ball.

12. The biofouling monitor of claim 6, further comprising:
   g) a second column having an inlet and an outlet;
   h) optionally a microorganism nutrient feed line located upstream of said inlet of the second column;
   i) a third pressure sensor located upstream of said inlet of the second column for measuring flow pressure and a fourth pressure sensor located downstream of said outlet of the second column for measuring said flow pressure;
   j) a second recirculation system connected to the inlet of the second column, downstream of said feed line, and connected to the outlet of the second column for maintaining a pressure feed through said second column; and
   k) inert packing material located in said second column in an amount to permit the passing of a liquid containing material.

13. The biofouling monitor of claim 6, wherein said outlet is connected to a holding tank.

14. The biofouling monitor of claim 6, wherein said inlet draws an aqueous solution from an aqueous containing system and said outlet exits at least a portion of said aqueous solution back into said aqueous system at a point downstream of where said inlet is drawing from said aqueous system.

15. A method to monitor or detect biofouling ahead of time in an aqueous solution comprising:
   a) passing at least a portion of said aqueous solution on a continuous basis through a column having an inlet and an outlet;
   b) introducing a microorganism nutrient into said portion of said aqueous solution at a point upstream of said inlet;
   c) measuring flow pressures of said portion of said aqueous solution through said column at a first point before said inlet and at a second point after said outlet on a continuous or non-continuous basis;
   d) determining pressure differential based on measurements from said first point and said second point; and
   e) correlating said measurements to determine advance biofouling occurring in said aqueous solution.

16. The method of claim 15, wherein said aqueous solution is from an industrial water circuit.

17. The method of claim 15, wherein said aqueous solution is from a paper making water circuit.

18. The method of claim 15, wherein said column is a column made from plastic, glass, a ceramic material, or a metal.

19. The method of claim 15, wherein said microorganism nutrient feed line contains a glucose, pyruvate, or starch formulation.

20. The method of claim 15, further comprising an inert packing material located within said column and in an amount to permit the passing of a liquid containing material through said column.

21. The method of claim 15, wherein said inert packing material comprises rocks, glass, non-corrosive metal, ceramic material, or combinations thereof.

22. The method of claim 15, wherein said inert packing material is at least one stainless steel ball.

* * * * *

UNITED STATES PATENT AND TRADEMARK OFFICE
CERTIFICATE OF CORRECTION

PATENT NO.    : 6,311,546 B1
DATED         : November 6, 2001
INVENTOR(S)   : McNeel et al.

It is certified that error appears in the above-identified patent and that said Letters Patent is hereby corrected as shown below:

<u>Title page,</u>
Item [75], Inventors, delete "Ghent" and insert -- Gent --.

Signed and Sealed this

Second Day of April, 2002

Attest:

Attesting Officer

JAMES E. ROGAN
Director of the United States Patent and Trademark Office